US012059212B2

United States Patent
Murphy et al.

(10) Patent No.: US 12,059,212 B2
(45) Date of Patent: Aug. 13, 2024

(54) SYSTEMS AND METHODS FOR REGISTERING AND TRACKING ANATOMICAL STRUCTURES

(71) Applicant: Stephen B. Murphy, Winchester, MA (US)

(72) Inventors: Stephen B. Murphy, Winchester, MA (US); Douglas E. Hudson, Hopkinton, MA (US)

(73) Assignee: Stephen B. Murphy, Winchester, MA (US)

( * ) Notice: Subject to any disclaimer, the term of this patent is extended or adjusted under 35 U.S.C. 154(b) by 535 days.

(21) Appl. No.: 17/187,456

(22) Filed: Feb. 26, 2021

(65) Prior Publication Data

US 2022/0273372 A1 Sep. 1, 2022

(51) Int. Cl.
*A61B 34/20* (2016.01)
*A61B 90/00* (2016.01)
(Continued)

(52) U.S. Cl.
CPC .............. *A61B 34/20* (2016.02); *A61B 90/36* (2016.02); *A61B 90/96* (2016.02); *G06K 7/1417* (2013.01);
(Continued)

(58) Field of Classification Search
CPC ......... A61B 34/20; A61B 90/36; A61B 90/96; A61B 2034/2055; A61B 2034/2065;
(Continued)

(56) References Cited

U.S. PATENT DOCUMENTS 7,885,705 B2  2/2011  Murphy
8,267,938 B2  9/2012  Murphy
(Continued)

FOREIGN PATENT DOCUMENTS

DE   10 2015 212 352 A1   1/2017
EP          2266075 B1       9/2019

OTHER PUBLICATIONS

"Coordinate Systems," Microsoft, Coordinate Systems—Mixed Reality, Microsoft Docs, <https://docs.microsoft.com/en-us/windows/mixed-reality/design/coordinate-systems>, Feb. 24, 2019, pp. 1-12.
(Continued)

*Primary Examiner* — Joel Lamprecht
(74) *Attorney, Agent, or Firm* — Cesari and McKenna, LLP; Michael R. Reinemann

(57) ABSTRACT

An instrument registers and tracks a portion of a patient's anatomy by an Augmented Reality (AR) device worn by a surgeon during a surgical procedure. The instrument may be attached to the patient's anatomy. The instrument may be a tripod with a platform. A target plate having front and back faces may be securely attached to the platform. A two-dimensional (2D) code detectable by the AR device may be presented on the front and back faces of the target plate. The 2D code may define a coordinate system having a known relationship to a coordinate system for the patient's anatomy, e.g., through a transformation matrix. The AR device may utilize the coordinate system for the detected 2D code and the transformation matrix to present holograms in predetermined positions relative to the patient's anatomy.

20 Claims, 8 Drawing Sheets

(51) Int. Cl.
  *A61B 90/96* (2016.01)
  *G06K 7/14* (2006.01)
(52) U.S. Cl.
  CPC ............... *A61B 2034/2055* (2016.02); *A61B 2034/2065* (2016.02); *A61B 2090/365* (2016.02)
(58) Field of Classification Search
  CPC ........ A61B 2090/365; A61B 2034/102; A61B 2034/105; A61B 34/25; A61B 90/39; A61B 17/02; A61B 2090/372; A61B 2090/3983; A61B 2090/502; G06K 7/1417; A61F 2/32
  See application file for complete search history.

(56) References Cited

U.S. PATENT DOCUMENTS

| | | | |
|---|---|---|---|
| 9,861,446 B2 | 1/2018 | Lang | |
| 10,016,287 B2 | 7/2018 | Murphy et al. | |
| 2009/0306679 A1 | 12/2009 | Murphy | |
| 2014/0358151 A1 | 12/2014 | Murphy et al. | |
| 2016/0278868 A1* | 9/2016 | Berend | A61B 5/1127 |
| 2018/0185100 A1* | 7/2018 | Weinstein | A61F 2/461 |
| 2020/0375666 A1 | 12/2020 | Murphy | |

OTHER PUBLICATIONS

"Device Tracking Overview," PTC Inc., Vuforia Developer Library, <https://library.vuforia.com/features/environments/device-tracker-overview.html>, retrieved on Feb. 20, 2021, pp. 1-4.

"QR Code Tracking," Microsoft, QR Code Tracking—Mixed Reality, Microsoft Docs, <https://docs.microsoft.com/en-us/windows/mixed-reality/develop/platform-capabilities-and-apis/qr-code-tracking>, Jan. 21, 2021, pp. 1-12.

"Datalogic: Reference Guide Laser Marking Systems," Jun. 1, 2019, Retrieved from the Internet: URL: <https://cdn.datalogic.com/upload/res/literature/ReferenceGuides/RG-Laser-Marking-ENA4.pdf>, Retrieved on Jul. 15, 2020, pp. 1-52.

"Notification of Transmittal of the International Search Report and the Written Opinion of the International Searching Authority, or the Declaration," International Filing Date: Feb. 16, 2022, International Application No. PCT/US2022/016515, Applicant: Surgical Planning Associates Inc., Date of Mailing: Jun. 7, 2022, pp. 1-17.

Zhao, Yin, et al., "An Analysis in Metal Barcode Label Design for Reference," FITEE, Frontiers of Information Technology & Electronic Engineering, Zhejiang University Press and Springer-Verlag Berlin, Heidelberg, vol. 17, No. 2, Feb. 6, 2016, pp. 173-184.

\* cited by examiner

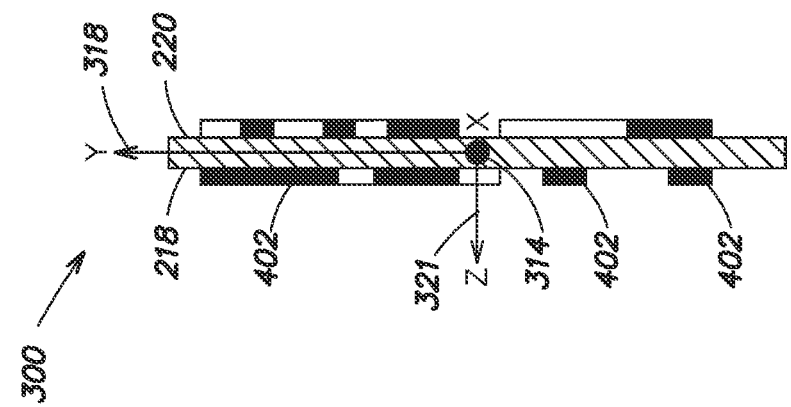
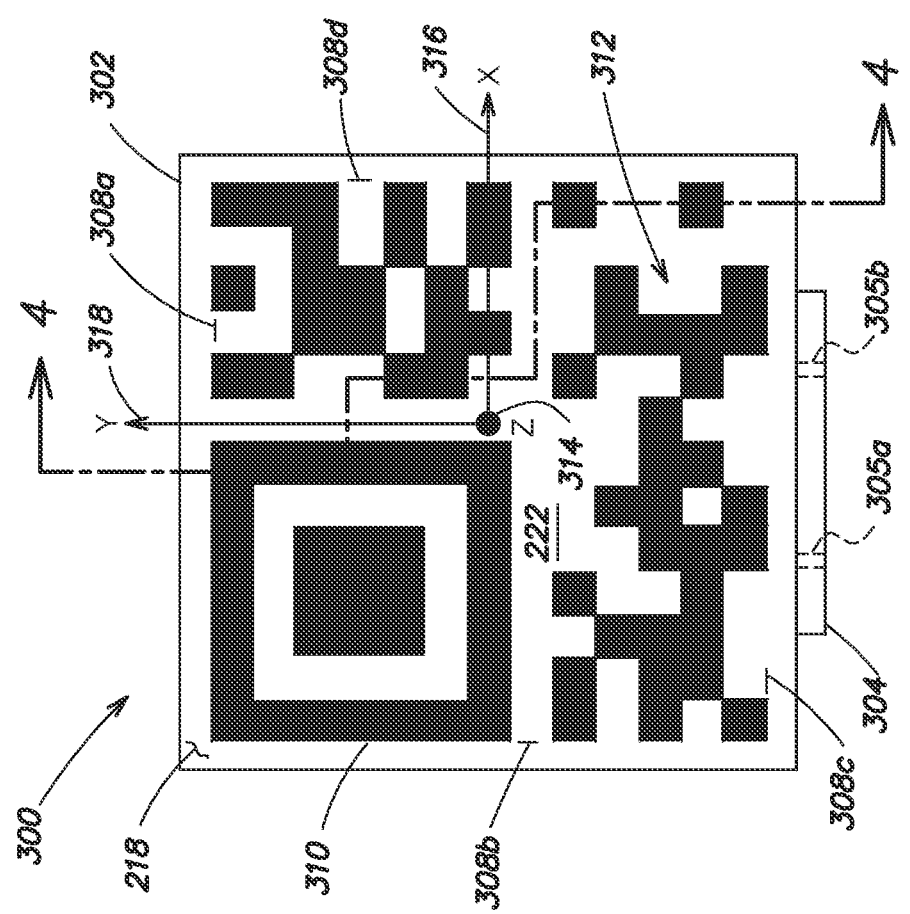
FIG. 4
FIG. 3

SYSTEMS AND METHODS FOR REGISTERING AND TRACKING ANATOMICAL STRUCTURES

BACKGROUND

Technical Field

The present disclosure relates to systems and methods for conducting navigation during surgery.

Background Information

During orthopedic implant procedures, e.g. total hip replacement (THR), the orientation of the surgical implants has a direct impact on the postoperative function and long term operability of the implant. Commercially available computer-assisted surgery systems use tracked tools using optical or magnetic tracking systems. These systems are able to track patient coordinate system accurately and reliably. However, the factors, such as high costs, limited operating range, maintaining a line of sight contact, magnetic interferences, are main issues associated with these technologies.

SUMMARY

The present disclosure relates to systems and methods for registering and tracking a portion of a patient's anatomy by an Augmented Reality (AR) device worn by a surgeon during a surgical procedure. The systems may include a registration instrument for attachment to the patient's anatomy. The instrument may be in the form of a tripod. For example, the instrument may include three legs supporting a frame. The frame may include a hub and two adjustable arms. One of the legs may extend from the hub and the other two legs may extend from the adjustable arms. A target plate having front and back faces may be fixedly attached to the frame. A code designed to be detected by the AR device may be placed on the front and back faces of the target plate. For example, a two-dimensional (2D) code may be placed on the front and back faces of the target plate. The 2D code may define a coordinate system. The coordinate system may have a known relationship to a coordinate system for the patient's anatomy. The AR device may utilize the coordinate system for the detected 2D code and a transformation matrix to present one or more holograms in predetermined positions relative to the patient's anatomy.

In some embodiments, the 2D code may be integrated with the target plate, such that the target plate and the 2D code form a single unit or structure. For example, instead of attaching a printed 2D code to the target plate, the target plate may be formed from aluminum that has been black anodized. The front and back faces may then be laser etched to create the 2D code. For example, block-shaped portions of the black anodized front and back faces may be laser etched to reveal the underlying aluminum. The contrast between adjacent blocks of black anodized surface and revealed aluminum substrate creates the 2D code. The integrated target plate and 2D code may be oversized to improve detection by the AR device. For example, the integrated target plate and 2D code may be approximately four inches by four inches. Furthermore, the 2D code formed in the target plate may have a simplified structure, for example it may only include one positioning detection marker. Because the 2D code is integrated in the target plate and they are formed from surgical grade metal, e.g., aluminum, it and the registration instrument can be repeatedly sterilized and reused without the 2D code and thus the information encoded therein becoming degraded.

BRIEF DESCRIPTION OF THE DRAWINGS

The description below refers to the accompanying drawings, of which:

FIG. 3 is a front view of a target plate of a registration and tracking instrument in accordance with one or more embodiments;

FIG. 4 is a highly schematic side view of the target plate of FIG. 3 along lines 4-4 in accordance with one or more embodiments;

DETAILED DESCRIPTION OF ILLUSTRATIVE EMBODIMENTS

Figure 1:
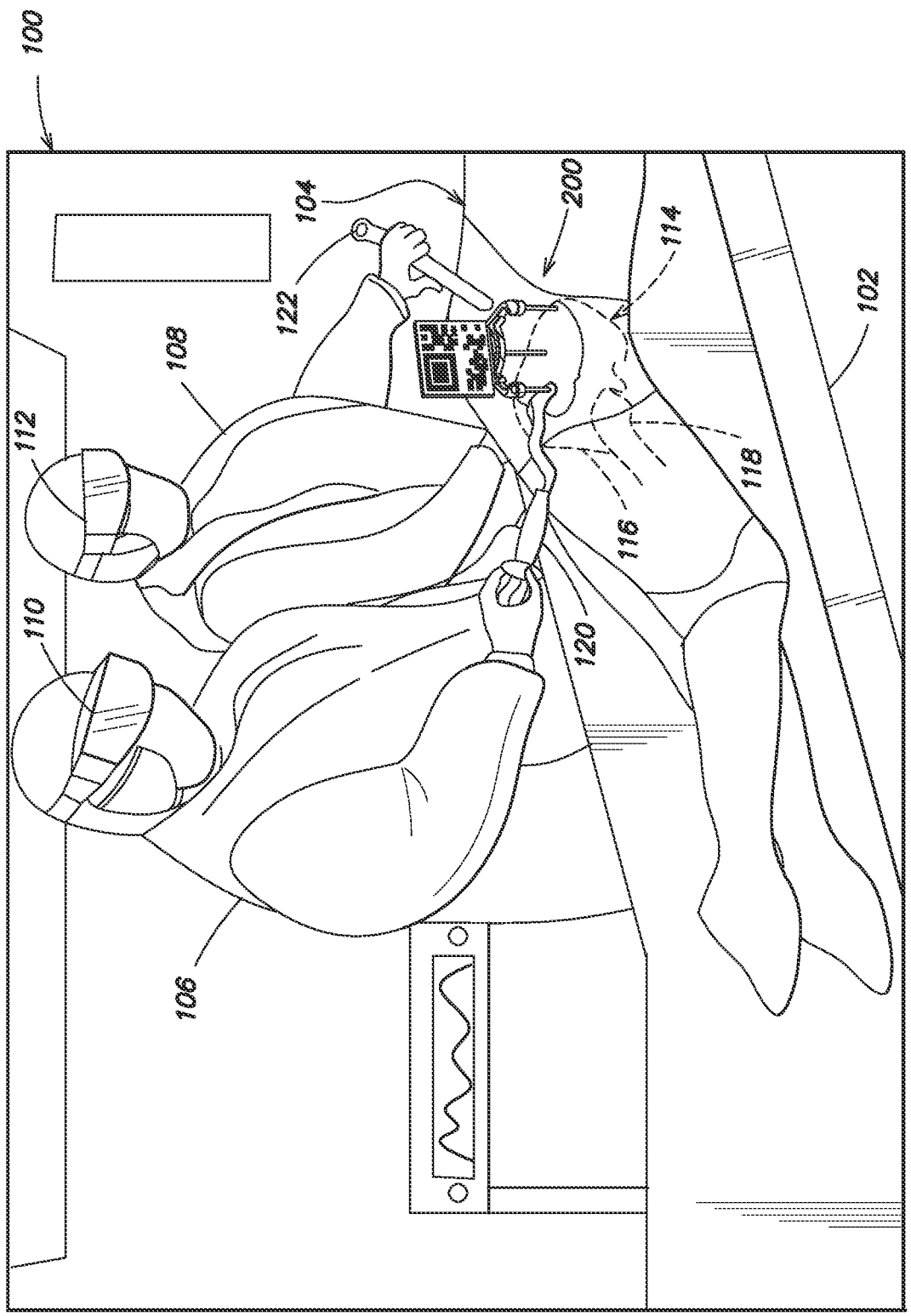
FIG. 1 is a schematic illustration of an operating room environment in accordance with one or more embodiments.

FIG. 1 is a schematic illustration of an operating room environment 100 in accordance with one or more embodiments of the present disclosure. Disposed in the operating room 100 is an operating table 102 on which a patient 104 is positioned for a surgical procedure. One or more surgeons and/or assistants may be in the operating room 100, such as surgeons 106 and 108. One or more of the surgeons 106 and 108 may be wearing an Augmented Reality (AR) device, such as AR headsets or head mounted devices (HMDs) 110 and 112 worn by the surgeons 106 and 108, respectively.

The patient 104 may be undergoing a Total Hip Replacement (THR) procedure on his right hip indicated in phantom generally at 114. The patient 104 may be lying on the operating table 102 in a lateral position. For example, the patient 104 may be lying on his left side, thus exposing his right hip 114. Also shown in phantom are the patient's pelvis 116 and his right femur 118. To perform the THR procedure the surgeons 106 and 108 may use one or more surgical instruments and may implant one or more prosthetic components in the patient 104. For example, the surgeon 106 is using a cup impactor instrument 120, which may be used to implant a prosthetic cup component in the patient's acetabulum. The surgeon 108 is using a retractor 122 to provide access to the patient's right hip 114, e.g., through an incision.

In some embodiments, the choice of specific prosthetic components and the locations and orientations, e.g., positions, at which they are to be implanted in the patient 104 may be determined by the surgeons 106 and 108 ahead of the surgical procedure. The planned positions of the prosthetic components may be determined relative to a coordinate frame or system. Exemplary coordinate frames or systems include the Anterior Pelvic Plane (APP). To ensure that the prosthetic components are placed at the planned positions, a portion of the patient's anatomy may be registered during the surgical procedure. For example, the patient's pelvis 116 may be registered during the procedure. In some embodiments, the patient's pelvis 116 may also be tracked. In order to register the patient's pelvis 116, an instrument 200 may be docked to the patient's right hip 114. The instrument 200 may be docked to the patient's pelvis 116 in a planned and thus known position. The instrument 200 may also track the patient's pelvis 116, e.g., during the surgical procedure. The instrument 200 may be referred to as a registration and tracking instrument.

The AR headsets 110 and 112 may present information to the surgeons 106 and 108 during the surgical procedure. For example, the AR headsets 110 and 112 may present holograms of at least portions of the patient's anatomy that may be hidden, e.g., below the patient's skin. For example, the AR headsets 110 and 112 may present holograms of the patient's pelvis 116 and/or femur 118. The AR headsets 110 and 112 may also present information that assists the surgeons 106 and 108 in implanting the prosthetic components at the desired, e.g., planned, positions. For example, the AR headsets 110 and 112 may present holograms of the positions of surgical instruments for preparing the patient's anatomy to receive the prosthetic components. The surgeons 106 and 108 may move physical instruments so that they are aligned with the holograms. The AR headsets 110 and 112 may also present holograms of the prosthetic components at the desired, e.g., planned locations. The surgeons 106 and 108 may implant the prosthetic components so that they are aligned with the holograms. The AR headsets 110 and 112 may cause these holograms to appear in locations based on registration information provided by the instrument 200. That is, the AR headsets 110 and 112 may be configured to operate as surgical navigation systems.

Suitable AR devices include the HoloLens series of mixed reality devices from Microsoft Corp. of Redmond, WA, the Magic Leap One device from Magic Leap, Inc. of Plantation, FL, and the Blade smart glasses from Vuzix Corp. of West Henrietta, NY, among others.

Figure 2:
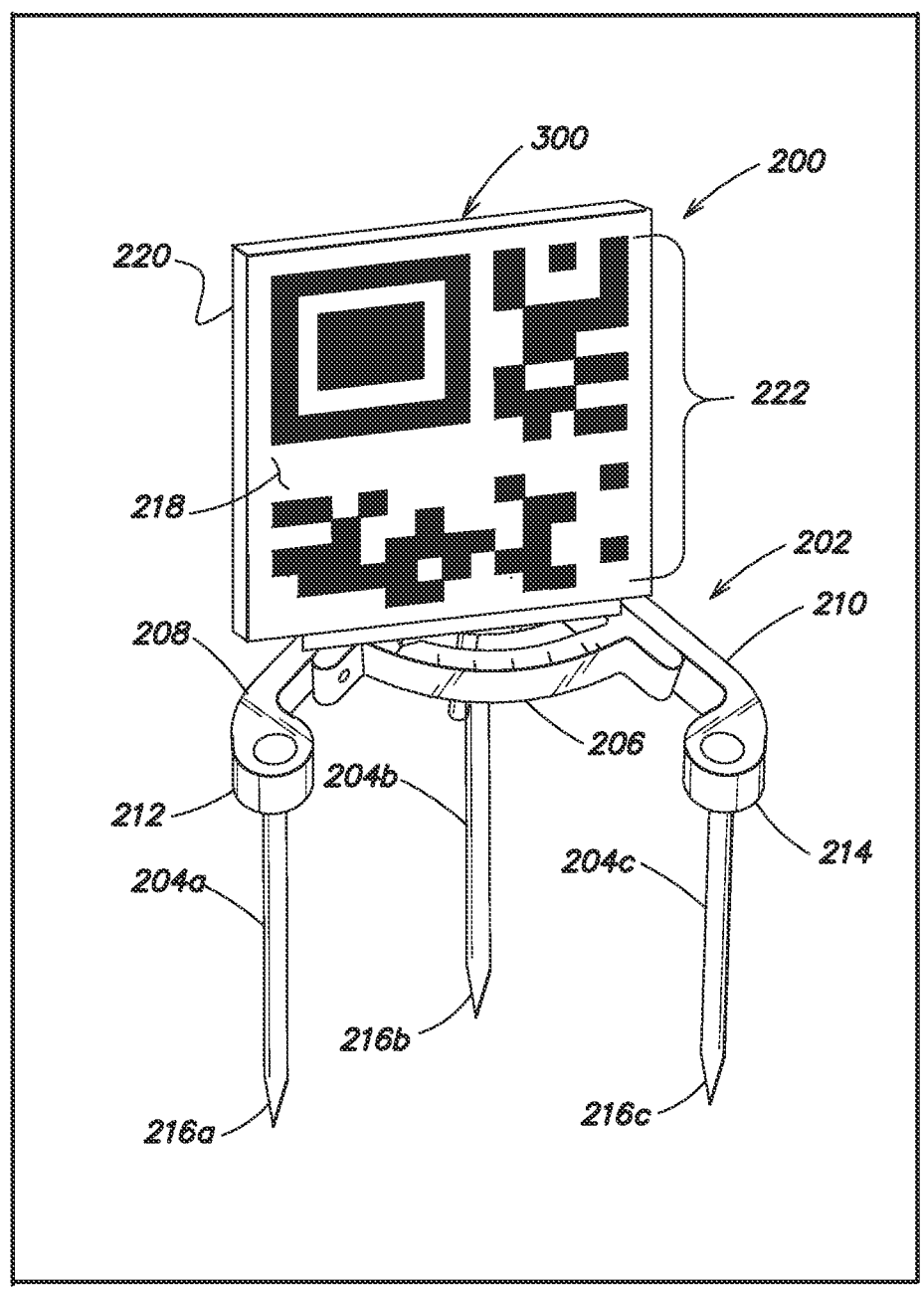
FIG. 2 is a perspective view of the registration and tracking instrument 200 in accordance with one or more embodiments.

FIG. 2 is a perspective view of the registration and tracking instrument 200 in accordance with one or more embodiments. The instrument 200 may include a platform indicated at 202 that is supported by a plurality of legs, such as three legs 204a-c. The platform 202 may include a central hub 206 and two arms 208 and 210 that extend from the hub 206 at an acute angle relative to each other. The arms 208 and 210 may include ends 212 and 214, respectively, opposite the hub 206. Legs 204a and 204c may extend from the ends 212 and 214 of the arms 208 and 210. The leg 204b may extend from the hub 206. The instrument 200 may thus be in the form of a tripod.

The legs 204a-c may include tips 216a-c, respectively, and the platform 202 may be generally planar and thus define a nominal plane. In some embodiments, the legs 204a-c may be of different lengths. As a result, the nominal plane of the platform may not be parallel to a plane defined by the tips 216a-c of the three legs 204a-c. In other embodiments, the legs 204a-c may all be of the same length and thus the nominal plane defined by the platform 202 may be parallel to the plane defined by the tips 216a-c of the three legs 204a-c.

In some embodiments, the one or more of the arms 208 and 210 may be adjustable relative to the hub 206. That is, the ends 212 and 214 of the arms 208 and 210 may be extended away from the hub 206 and may also be retracted toward the hub 206. By adjusting the lengths of the arms 208 and 210, the distances between the tips 216a-c of the legs 204a-c may be adjusted. At least one and preferably all of the legs 204a-c may be removable from the platform 202. The instrument 200 may include other components, such as locking or set screws to secure the arms 208 and 210 at desired extension positions. Additional locking or set screws may be used to secure the legs 204a-c to the arms 208 and 210 and the hub 206.

It should be understood that the instrument 200 may take other forms. It should also be understood that the instrument may include locking screws to secure the arms to the hub at the desired extension.

The instrument 200 also may include a target plate 300 mounted to the platform 202 opposite the legs 204a-c. The target plate 300 may be substantially planar and include a front face or surface 218 and a back face or surface 220. In some embodiments, the target plate may be symmetrically disposed on the platform 202, e.g., on the hub 206.

A two-dimensional (2D) code indicated at 222 may be presented on the front face 218. The 2D code 222 may be formed from an arrangement of black and white blocks. For example, the 2D code 222 may be formed from a plurality of black and white pixels. Although not shown in FIG. 2, a 2D code may also be presented on the back face 220 of the target plate 300. These two codes, moreover, may be different from each other. That is, the arrangement of pixels may be different.

In some embodiments, the target plate 300 may be square. However, it should be understood that the target plate 300 may take other two-dimensional shapes, such as rectangular, oval, round, etc. The target plate 300 may be mounted orthogonally to the nominal plane of the platform 202. The target plate 300 may be securely attached to the platform 202. Nonetheless, the target plate 300 may be removable, e.g., to aid in sterilization of the instrument 200.

FIG. 3 is a front view of the target plate 300 in accordance with one or more embodiments. The target plate 300 may include a panel 302 and a base 304. The panel 302 may extend upward from the base 304, e.g., at 90 degrees. The base 304 may include holes indicated at 305a and 305b for receiving screws, pins, or other fasteners in order to securely attach the target plate 300 to the instrument 200.

The panel 302 may include the front face 218 of the target plate 300 and the back face 220 of the target plate 300. The front and back faces 218 and 220 may present one or more two-dimensional (2D) codes or patterns, such as the 2D code 222 on the front face 218. As noted, the 2D codes or patterns on the front and back faces 218 and 220 may be different from each other.

Referring to FIG. 3, the 2D code 222 may be formed by a plurality of pixels. The pixels may have one of two possible settings, namely black or white. However, it should be understood that other settings or colors having strong contrast may be used, such as black and silver, dark blue, dark purple, or dark brown and silver, etc. In some embodiments, the panel 302 may be a square, and may be on the order of four inches by four inches. The panel 302 may be approximately 0.20 inches thick. It should be understood that the panel 302 may have other dimensions and thicknesses. For example, it may be greater or lesser than four by four inches, and greater or lesser than 0.20 inches thick. The 2D code 222 may fill the four inch by four inch panel 302 and may comprise less than 20 by 20 and preferably 15 by 15 or 14 by 14 pixels. It should be understood that other pixel array sizes may be used.

The 2D code 222 may include a plurality of structure elements. In some embodiments, the 2D code 222 may include three structure elements. For example, the 2D code 222 may include a quiet zone or margin consisting of a top border 308a, a left border 308b, a bottom border 308c, and a right border 308d, a positioning detection marker 310, and a detection pattern indicated at 312. The quiet zone 308a-d may be located along an outer edge of the panel 302. The quiet zone 308a-d may define an outer border of the 2D code 222. The quiet zone 308a-d may be one pixel in width and may be entirely white. In some embodiments, the 2D code 222 may include just one, single positioning detection marker, e.g., marker 310, which may be located in an upper left corner of the 2D code 222, as illustrated.

The detection pattern 312 may include a plurality of black and white pixels or blocks arranged in a predetermined pattern. In some embodiments, the detection pattern 312 may be a simple rather than complex pattern. For example, the detection pattern may include several groups of white pixels and/or groups of black pixels coalesced into larger shapes. At least some of the groups may include five, six, seven or more adjoining or adjacent pixels coalesced into a contiguous shape. By including such shapes of coalesced pixels, the detection pattern 312 may have a simple structure.

In some embodiments, the 2D code 222 may be limited to just having the quiet zone or margin 308a-d, the one positioning detection marker 310, and the detection pattern 312. The detection pattern 312 may take up the entire 2D code 222, except for the quiet zone 308a-d and the positioning detection marker 310.

While superficially similar to a Quick Response (QR) code, the 2D code or pattern 222 of the present disclosure is not a QR code. For example, a QR code includes three positioning detection markers or patterns. In contrast, the 2D code 222 of the present disclosure may only include one such marker or pattern 310, e.g., in the upper left corner. A QR code also includes alignment markings, timing patterns, version information, format information, and error correction codes. In some embodiments, the 2D code 222 of the present disclosure does not include any alignment markings, timing patterns, version information, format information, or error correction codes. A QR code also encodes data or information, such as a Uniform Resource Locator (URL). The data elements of the detection pattern 312 of the 2D code 222 may not encode any data or information. Thus, the 2D code 222 of the present disclosure may not be readable or otherwise decipherable by a QR scanner.

As described herein, a spatial coordinate system may be associated with the 2D code 222, and the AR headsets 110 and 112 upon detecting the 2D code 222 in the operating room environment 100 can access the spatial coordinate system associated with the detected 2D code 222. The coordinate system may include an origin 314 and three orthogonal axes, such as an x-axis 316, a y-axis 318, and a z-axis 321 (FIG. 4). In some embodiments, the origin 314 may be in the middle of the panel 302 on a line connecting the centers of the 2D codes on the front and back surfaces 218 and 220. That is, the origin 314 may be halfway between the front and back faces 218 and 220. As noted, the panel 302 may be 0.20 inches thick. The x-axis 316 may point to the right, the y-axis 318 may point up, and the z-axis 320 may point out of the paper.

The blocks or pixels of the 2D code 222 may be aligned in rows and columns that are orthogonal to each other. The x-axis 316 and the y-axis 318 may be aligned with these rows and columns. Furthermore, the 2D code 222 is planar and the z-axis 321 may extend at a right angle to the plane of the 2D code 222. The origin 314, moreover, may be located by determining the center of the 2D code 222. The spatial coordinate system is thus aligned with the 2D code 222. That is, the spatial coordinate system can be derived upon detecting the 2D code 222 in space.

It should be understood that the origin 314 of the spatial coordinate system associated with the 2D code 222 may be positioned at other locations besides the center of the 2D code 222, such as the top left corner, the bottom left corner, etc.

In some embodiments, one or more computer program applications (apps) may be created and loaded onto the AR headsets 110 and 112. The apps may include a planning application for running a surgical plan created for a patient and a navigation application for detecting a 2D code, deriving the coordinate system associated with the detected 2D code, and utilizing a transformation matrix to present and anchor one or more holograms at planned positions.

The navigation app running on the AR headsets 110 and 112 may be configured to associate the 2D codes on the front and back faces 218 and 220 with the coordinate system. For example, the navigation app may associate the 2D code 222 on the front surface 218 as illustrated in FIG. 3, i.e., with the x-axis 316 pointing to the right, the y-axis 318 pointing up, and the z-axis 321 pointing out of the paper. The navigation app may associate the 2D code on the back surface 220 (which is a different code than on the front, namely it has a different detection pattern) with the coordinate system as seen from the back surface 220. For example, the navigation app may associate the 2D code on the back surface 220 such that the x-axis 316 points to the left, the y-axis 318 points up, and the z-axis 321 points into the paper.

The detection patterns of the 2D codes on the front and back surfaces 318 and 320 of the target plate 300 should be significantly different from each so that the navigation app may clearly distinguish between the two 2D codes.

The apps may be controlled through user interface elements provided the AR headsets 110 and 112, such as hand gestures for opening and interfacing with apps. In other embodiments, a surgeon may control and/or operate the apps using verbal commands. For example, in response to a first verbal command, e.g., "load", the app may automatically open a file explorer window. The surgeon can then select a hologram file in a subfolder with a hand gesture. The app may automatically access a transformation matrix for the hologram, which may also be located in the same folder, identify the physical 2D code in the surgical scene, and present and anchor the hologram. In other embodiments, the surgeon can use other verbal commands to cause the AR device to load and present additional holograms. Exemplary verbal commands include "hologram2", "hologram3", etc. for presenting the holograms in the planned order for the surgical procedure.

Suitable apps for use with the present disclosure are described in commonly owned, co-pending U.S. patent application Ser. No. 16/888,048, filed May 29, 2020, which application is hereby incorporated by reference in its entirety.

In other embodiments, the one, single positioning detection marker 310 of the 2D code 222 may be located at other positions, such as in the lower left corner or the upper right corner. In other embodiments, a second positioning detection marker or pattern or both second and third positioning detection markers may be included in the 2D code 222.

FIG. 4 is a cross-sectional view of the target plate 300 along the lines 4-4 of FIG. 3 in accordance with one or more embodiments. The target plate 300 may be anodized to produce an anodic oxide structure indicated at 402 on its outer surface. For example, the target plate 300 may be aluminum and the anodic oxide structure may be aluminum oxide. This aluminum oxide is not applied to or deposited on the surface like paint, coatings, or plating. Instead, the aluminum oxide is fully integrated with the underlying aluminum substrate. The aluminum oxide may be dyed black. The back face 220 may similarly include an aluminum oxide on its outer surface. Portions of the front and back faces 218 and 220 may be laser etched to form the respective 2D detection patterns, e.g., detection patter 222. For example, selected blocks or pixels of the black anodic oxide structure on the surface may be laser etched away revealing the underlying aluminum substrate. For example, the quiet zone 308a-d may be laser etched. Blocks or pixels that are laser etched, thus revealing the underlying aluminum substrate appear silver or white, while blocks or pixels that are not laser etched remain black due to the black anodic oxide structure on the outer surface.

It should be understood that FIG. 4 is a highly schematized drawing provided for explanation purposes and is not drawn to scale. Furthermore, while the anodic oxide structure is illustrated as separate from the aluminum substrate, as described herein the anodic oxide structure, i.e., the aluminum oxide is integral to the aluminum oxide.

Figure 5:
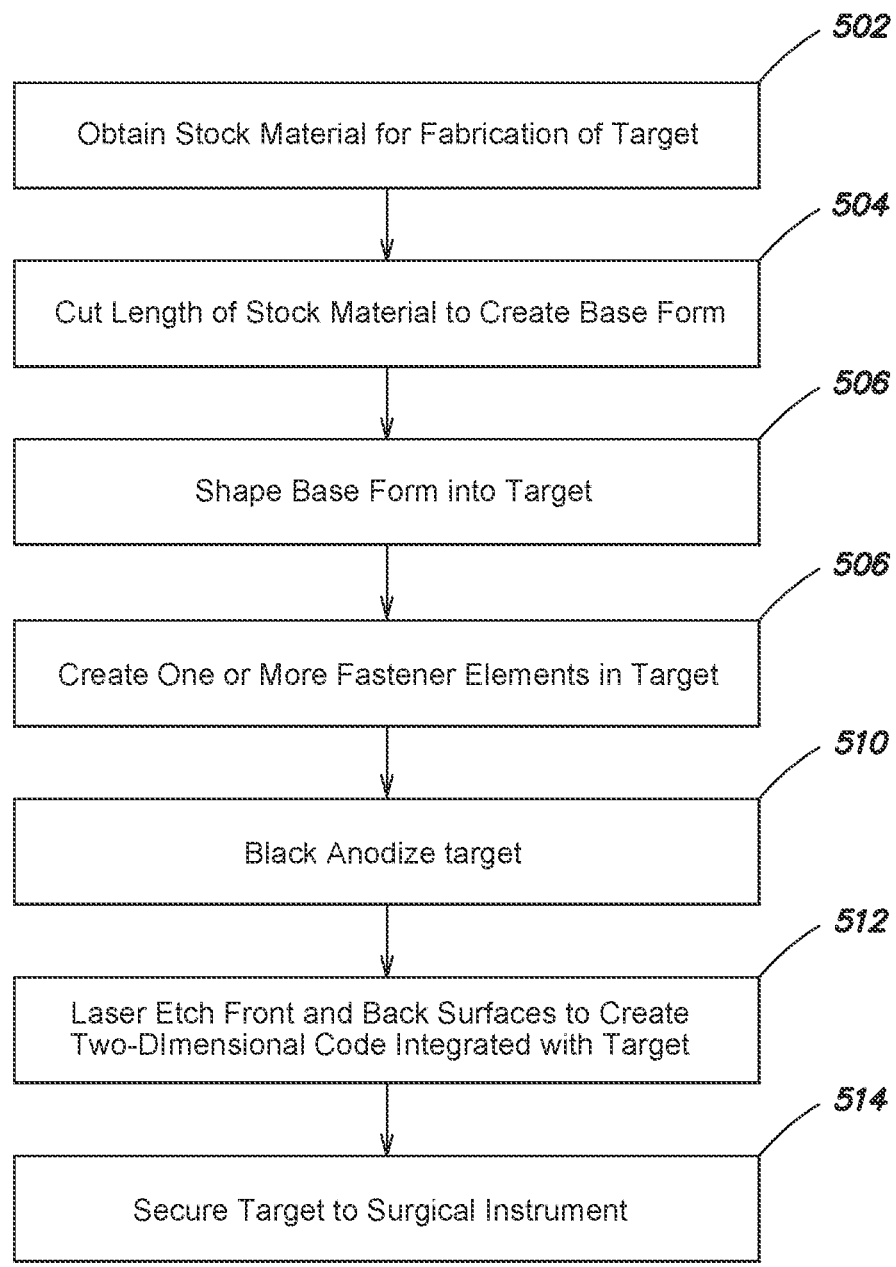
FIG. 5 is a flow diagram of an example method of fabricating a target plate in accordance with one or more embodiments.

FIG. 5 is a flow diagram of an example method of fabricating a target plate in accordance with one or more embodiments. Stock material may be obtained, as indicated at step 502. The stock material may be four-inch by four-inch aluminum, 90 degree (right) angle stock. A length of the angle stock material may be cut to produce a section or base form from which a target plate may be created, as indicated at step 504. For example, a four inch section may be cut from the angle stock. The section or base form may be shaped to form the panel and the base of the target plate, as indicated at step 506. In some embodiments, fastener elements, such as through holes, may be formed in the base, as indicated at step 508.

The formed target plate may be anodized, as indicated at step 510. The anodizing may be performed according to the Mil Spec MIL-A-8625 II standard, also referred to as common or standard anodizing. For example, the oxide coating may be created by placing the section of aluminum angle stock in a sulfuric acid bath while running a low-voltage DC current through the part to cathodes on the side of the tank. The aluminum acts as an anode in the electrical circuit, so that oxygen ions are released from the electrolyte to combine with the aluminum atoms at the surface of the part being anodized. The aluminum angle stock may be black anodized by dipping the part into a hot dye tank directly after anodizing. It should be understood that anodizing is very different than paints, plating and other common coatings on metal. While paints, plating and coatings sit on top of the surface of the material, e.g., aluminum, anodizing converts the outer layer of aluminum to aluminum oxide, so the coating is fully integrated with the aluminum substrate. The resulting oxide coating may be very thin, e.g., 0.00005 to 0.0005 inches thick.

It should be understood that black anodizing may also be performed according to the MIL-A-8625 III standard, also referred to as "hardcoat" anodizing.

It should be understood that other colors besides black may be used, such as dark blue, dark brown, dark gray, etc. The front and back faces of the panel may be laser etched to form the 2D codes or patterns on the front and back faces, as indicated at step 512. The target plate may be secured to the instrument, as indicated at step 514.

The 2D codes are thus integral to or with the target plate. That is, the 2D codes are not printed on paper and attached to the target plate, nor or they painted on the target plate. Instead, the target plate including the 2D codes constitutes a single, unitary object.

It should be understood that other materials that may be black anodized besides aluminum may be used to fabricate the target plate 300, such as magnesium and titanium.

Figure 7:
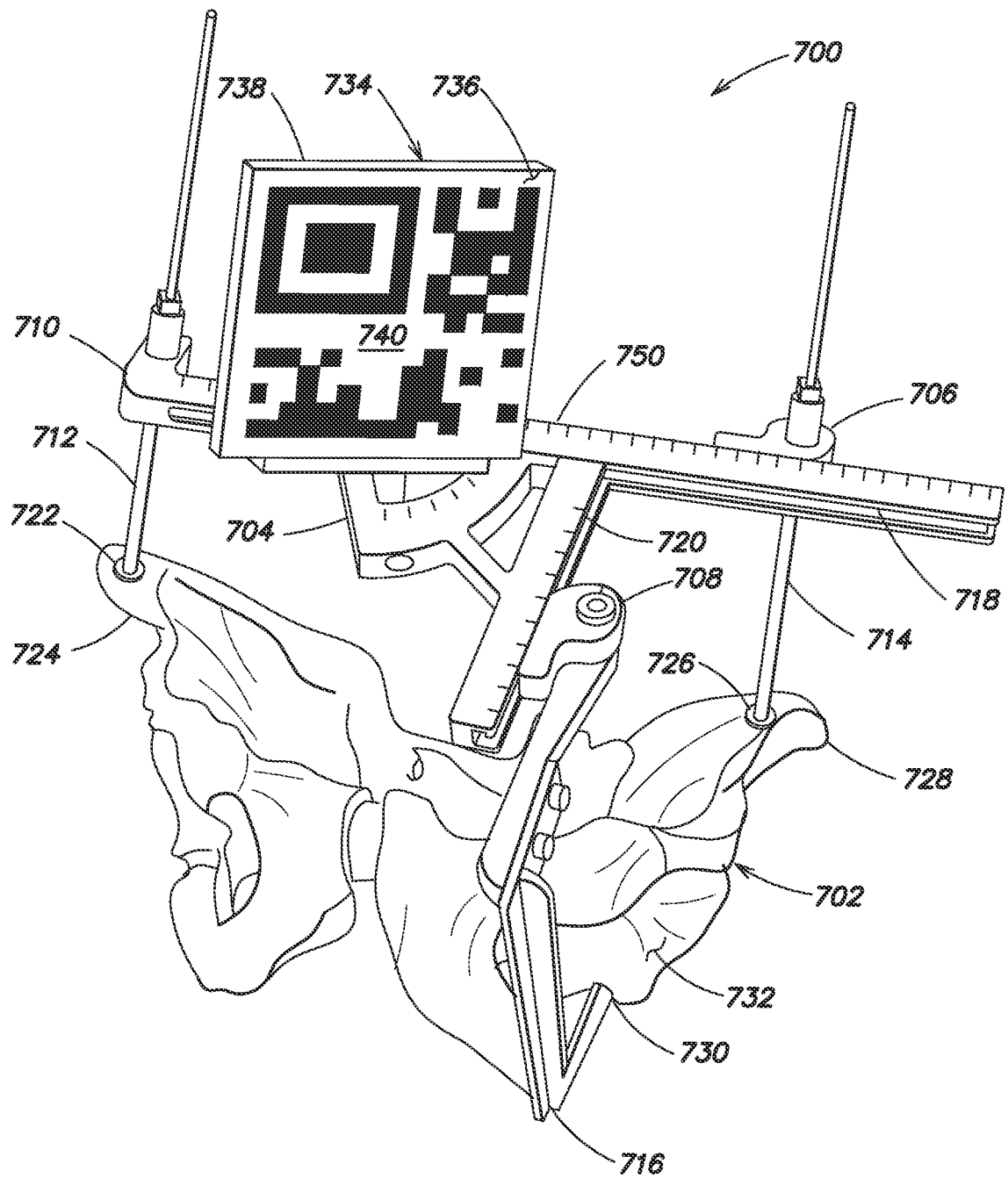
FIG. 7 is a perspective view of a registration and tracking instruments in accordance with one or more embodiments.

FIG. 7 is a perspective view of another hip registration and tracking instrument 700 docked to a pelvis 702 in accordance with one or more embodiments. The tool 700 may include an elongated support arm 750, a support frame 704, a first moveable leg brace 706, and a second moveable leg brace 708. The elongated support arm 750 may include a first end 710. Disposed at the first end 710 may be a first leg 712 that may extend perpendicularly from the support arm 750. A second leg 714 may be extend through the first moveable leg brace 706. A third leg 716, which may be C-shaped, may be attached to the second moveable leg brace 708. The second and third legs 714 and 716 may also extend perpendicularly from the elongated support arm 750, like the first leg 712.

A first track 718 may be formed along at least a portion of a front side of the support arm 750, and a second track (not shown) may be formed along at least a portion of a back side of the support arm 750. The first and second tracks may be recessed tracks, such as slots or grooves. The support frame 704 may include a first edge that engages the first track 718 securing the support frame 704 to the elongated support arm 750, while allowing the support frame 704 to slide along the front side of the elongated support arm 750. The first moveable leg brace 706, and thus the second leg 714, may be configured for slidable attachment to the back side of the elongated support arm 750. The support frame 704 may include a second edge 720 to which the second moveable leg brace 708 may slidably attach.

The first leg 712 may have a 722 tip configured to contact the right ASIS 724 of the pelvis 702. As described, the second and third legs 714 and 716 may be slidably attached to the elongated support arm 750 relative to the first leg 712. The distances between the first leg 712 and the second and third legs 714 and 716 may be determined preoperatively so that, when the second and third legs 714 and 716, are set to these predetermined distances along the elongated support arm 750, a tip 726 of the second leg 714 contacts the left ASIS 728 of the pelvis 702, and a tip 730 of the third leg 716 is received in the acetabulum 732 of the hip being operated on. An operating surgeon may access the patient's hip joint using the anterior approach or the anterolateral approach (e.g., with the patient in the supine position), and may dock the apparatus instrument 700 to the patient, thereby registering the patient's pelvis and establishing the patient-specific, supine pelvic reference plane and/or coordinate system.

Mounted to the support frame 704 may be a target plate 734. The target plate 734 may be substantially planar and include a front face 736 and a back face 738. A two-dimensional (2D) code indicated at 740 may be presented on the front face 736.

The instrument 700 may be flipped over so that it may be used to operate on a patient's left or right hips. The support frame 704 and the target plate 734 may also be flipped around so that it remains on top of the instrument 700. In some embodiments, the target plate may be at a 45 degree angle to the support arm 750, e.g., so that it faces the surgeon. The base of the target plate may have additional attachment holes so that it may be flipped around with the instrument 700.

Planning Stage

Obtain Image or Other Data

A patient may be diagnosed with a medical condition that requires surgery. For example, a patient may be diagnosed with hip joint failure, and may require total hip replacement (THR) surgery. In preparation for the surgical procedure, one or more data gathering procedures may be performed. For example, image data may obtained for a patient who is to undergo THR surgery. The image data may be obtained of that portion of the patient's anatomy on which the surgery is to be performed, e.g., the left or right hip. One or more imaging systems may be used to obtain the patient-specific, pre-operative image data, such as such Computed Tomography (CT) data, Magnetic Resonance Imaging (MRI) data, conventional radiographs (X-rays), bi-planar or multiplanar simultaneous radiographs, or ultrasonic images. For example, one or more of Computed Tomography (CT), Magnetic Resonance Imaging (MRI), conventional radiographs (X-rays), bi-planar or multiplanar simultaneous radiographs, or ultrasonic images, may be taken of the patient. The one or more digital images (CT, magnetic, radiographic, ultrasonic, etc.) may provide three-dimensional (3D) information regarding the surface and/or structure of the portion of the patient's anatomy being operated on, e.g., the patient's hip.

The 3D information may be generated in other ways. For example, the 3D surface and/or structure of a patient's hip may be predicted or derived from a single image, a statistical model, one or more measurements taken of the patient's hip, etc.

Create Surgical Plan

Next, a surgical planner, such as an experienced surgeon or other person, may create a surgical plan that may be specific to the patient. The surgical plan may be created using a computer-based planning tool. The planning tool may include a 3D modeling utility, and the surgical planner may access the one or more digital images providing the 3D information. The surgical planner may utilize the 3D modeling utilize to create a computer-generated, 3D model of the patient's anatomy being operated on, such as the patient's hip or portion thereof.

Using the 3D model (or a statistically based 3D model), one or more reference coordinate systems may be established for at least a portion of the patient's anatomy. Exemplary reference coordinate systems for the hip include the Anterior Pelvic (AP) plane coordinate system, the coordinate system of the raw CT data, a femoral coordinate system, a tibial coordinate system, etc. For example, a set of points on the 3D model of the patient's pelvis may be selected to define the AP plane coordinate system or another reference coordinate system.

The surgical plan may specify one or more prosthetic components to be implanted in the patient's body as well as the component's locations and orientations, e.g., positions. For example, the surgical plan may specify a particular prosthetic cup component and its position at a patient's acetabulum, including a depth, and an orientation within the acetabulum. The plan may also include the shape of the cup bed to receive the cup component. For example, the surgical plan may specify a particular volume or portion of bone in and/or around the patient's acetabulum that is to be removed, e.g., reamed, in order to receive the acetabular cup component. It may also specify a desired position of a prosthetic stem component at the patient's femur. Additionally or alternatively, the surgical plan may specify a value or a limit for one or more pre and post operative conditions, such as a limit for acceptable leg length and offset changes, and values for flexion, abduction, femoral anteversion, and/or combined anteversion.

In some embodiments, the plan may incorporate 3D models of one or more other tools, such as the registration and tracking instrument 200, acetabular reamers and cup impactors, among others. For example, the surgical planner may determine the location of an acetabular reamer at the 3D model of the pelvis to prepare the cup bed as planned. For example, the acetabular reamer may have a handle defining a longitudinal axis. The surgical planner may position a 3D model of the acetabular reamer so that the cutting basket of the reamer is positioned in the acetabulum to prepare the cup bed as planned. The surgical planner also may determine the location of a cup impactor at the 3D model of the pelvis to implant the cup component in the cup bed as planned. For example, the cup impactor may have a handle defining a longitudinal axis. The surgical planner may position a 3D model of the cup impactor so that the longitudinal axis defined by the handle positions the cup component at the end of the cup impactor in the cup bed as planned.

The planned positions of the selected implants and tools may be determined relative to the one or more reference coordinate systems established for the patient's anatomy, such as the AP plane coordinate system.

In some embodiments, the surgical plan may further include instructions for setting up and using the one or more registration instruments during the procedure, such as the instrument 200 (FIG. 2) or the instrument 700 (FIG. 7). The surgical plan may include a series of inputs or adjustments to be made to one or more registration instruments 200, 700 before or during the procedure. For example, the registration instruments 200, 700 may be adjustable, and the surgical planner may determine one or more inputs and/or adjustments to be made on the one or more registration instruments 200, 700 for use with the patient. The inputs and/or adjustments may be determined by fitting a model of the instrument 200, 700 to the 3D model of the patient's pelvis. Furthermore, knowledge of supine and/or standing pelvic tilt, which may be provided as part of the patient-specific information, can be incorporated in the adjustments to be made to the registration instrument 200, 700.

In particular, if the instrument 200 will be used, the surgical planner may plan where the legs 204*a-c* of the instrument 200 are to dock to the patient's pelvis. For example, the plan may provide that the tip 216*a* of the first leg 204*a* of the instrument 200 be positioned at a first point (referred to as the basepoint) located in the area of the posterior inferior acetabulum. The tip 216*c* of the second leg 204*c* may be positioned at a second point (referred to as the ASIS point) located in the area of the anterior superior iliac spine. The tip 216*b* of the third leg 204*b* may be positioned at a point located on the ilium, e.g., where the bone is dense. In some embodiments, the surgical planner may determine how far the arms 208 and 210 should be extended so that the legs 216*a-c* will dock at the planned points on the 3D model of the patient's pelvis.

If the instrument 700 will be used, determinations may be made regarding where the legs 712, 714 and 716 are to dock to the 3D model of the patient's pelvis.

Figure 6:
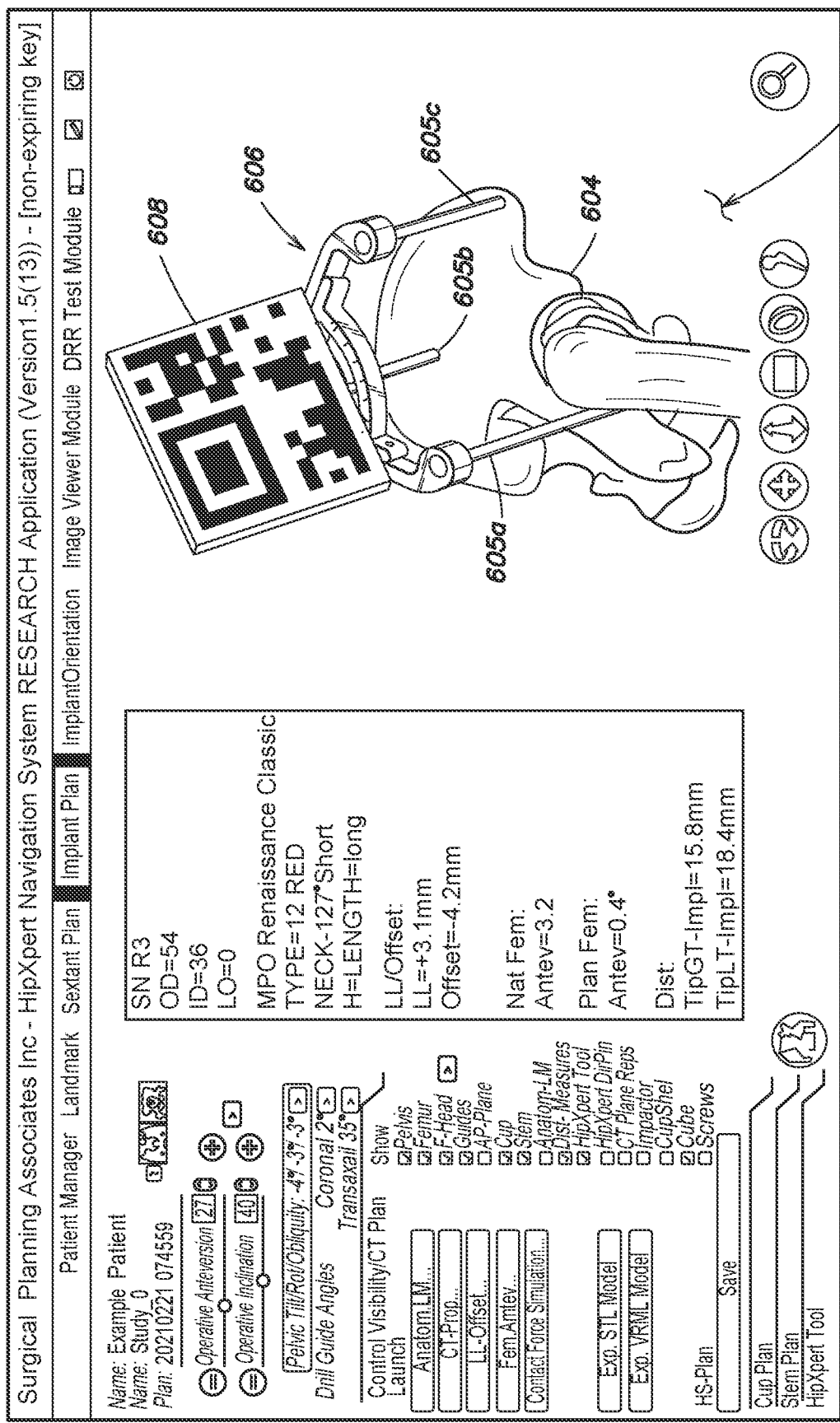
FIG. 6 is an illustration of a planning window in accordance with one or more embodiments.

FIG. 6 is an illustration of a planning window 600 generated by a planning tool and presented on a display of a workstation in accordance with one or more embodiments. The planning window 600 includes a model pane 602 presenting a 3D model of a patient's pelvis 604. Docked to the model of the pelvis 604 is a 3D model 606 of the registration and tracking instrument 200. The model 606 of the instrument may include legs 605a-c and a target plate 608. As described, the planner may determine one or more adjustments to the instrument 200 so that, when it is docked to the 3D model 604 of the patient's pelvis, the legs 605a-c contact the 3D model of the pelvis 604 at the planned points.

In some embodiments, the surgical plan for a THR procedure may include files of 3D models of one or more of:
the patient's pelvis (or portion thereof);
the patient's femur(s) (both alone and as part of the pelvis);
the registration instrument 200, 700 as customized for the patient (both alone and as positioned on the patient's pelvis);
a reamer tool positioned at the planned depth of the acetabulum and in the planned orientation for the cup component relative to the AP Plane coordinate system (or a sequence of reamer tools with different size cup reamers leading to a final one);
a hemispherical surface representing the exact position of the ideally prepared bone surface for receipt of the acetabular component;
a cup impactor tool at the planned position and orientation relative to the AP Plane coordinate system for the cup component;
the selected prosthetic cup component at the planned orientation and depth in the acetabulum relative to the AP Plane coordinate system;
the selected prosthetic cup component and liner at the planned orientation and depth in the acetabulum relative to the AP Plane coordinate system;
the prosthetic stem at the planned orientation and depth relative to the femoral coordinate system, and/or the tibial coordinate system; and/or
one or more tracking devices.

It should be understood that various combinations of the above-listed 3D models also may be created.

As described, the positions of the implants, registration instrument 200, 700, and surgical tools may be planned relative to the one or more reference coordinate systems established for the patient's anatomy, e.g., the pelvis, such as the AP plane coordinate system. The planning tool may generate a transformation matrix so that these positions may be translated to the coordinate system defined for the target plate 300, 734 of the registration instrument 200, 700.

For example, as the geometry of the instrument 200, represented in the planning window 600 by the model 606, including the target plate 608 is known, the planning tool can determine the geometric relationship between the coordinate system defined by the target plate 608 and the one or more reference coordinate systems established for the pelvis model 604, e.g., the AP plane coordinate system. For example, the legs 204a-c of the instrument 200 is known. Also, the position of the target plate 300 with the 2D code 222 as mounted on the platform 202 is known. The planning tool may generate a transformation matrix for translating between the one or more reference coordinate systems established for the pelvis and the spatial coordinate system for the instrument 200. The transformation matrix may translate coordinates in one coordinate system, e.g., the reference coordinate system, to coordinates in the other coordinate system, e.g., the spatial coordinate system defined at the target plate 300.

The planning tool may export at least some of the 3D model files of the surgical plan into a format compatible with the AR headsets 110 and 112 so that the AR headsets 110 and 112 may project holograms corresponding to the exported 3D model files. For example, one or more of the files representing the 3D objects may be exported and loaded into the memory of the AR headsets 110 and 112. Alternatively, the files representing the 3D objects may be stored at a server and the AR device 200 may be configured as a client capable of accessing those files from the server.

For hip surgery, the following sequence of holograms may be generated:
1. A hologram of the registration instrument 200, 700 tool and the pelvis;
2. A hologram of the registration instrument 200, 700, the pelvis, and the ideal acetabular cup bed;
3. A hologram of the registration instrument 200, 700 and the ideal cup bed without showing the pelvis;
4. A hologram of the registration instrument 200, 700, the pelvis, the ideal cup bed or the cup component, and the acetabular cup component impaction handle situated in the ideal orientation for implanting the cup component;
5. A hologram of the registration instrument 200, 700, the pelvis, and the metal acetabular cup component without the bearing insert in which the native pelvis has all osteophytes still in place, and
6. A hologram of the registration instrument 200, 700, the pelvis, the metal acetabular component, and the bearing insert.

Nonetheless, it should be understood that other and/or addition holograms may be generated and included. Exemplary additional holograms include: holograms of the acetabular reamer handle and each sequential reamer basket in the ideal location, one or more of the above holograms without the registration instrument 200, 700. When the surgeon places the actual reamer handle with the final reamer basket in exact overlap with the hologram of the same, then the cup preparation bed is in the planned place. Such additional holograms may have some advantages over above-described holograms 2 and 3 since the surgeon may be unable to see where the reamer is in space when preparing the bony cup bed. Using those holograms, the surgeon may have to ream, take the reamer out, and look into the incision to compare the real prepared bony cup bed surface to the hologram. If instead or in addition there is a hologram of the exact reamer handle and basket, the surgeon will be able to tell if the cup bed is correct by looking at overlapping holograms and reality mostly outside of the patient's body. This may be more convenient, among other advantages. Also, during cup impaction, instead of the above-described hologram 4 with an idealized straight cup impactor (for alignment only), there may be a hologram of the same exact planned cup impactor to be used in surgery with the same exact planned cup component also to be used in surgery. Then, when impacting the cup, the surgeon can line up not only the orientation of the cup component to be correct, but can also tell if the cup component is fully seated and if it is in the correct place.

Once completed, the one or more electronic surgical plans created by the surgical planner may be transmitted to the surgeon performing the procedure. For example, the one or more plans may loaded onto the AR headsets 110 and 112.

In some embodiments, one or more applications (apps) may be created and loaded on the AR headsets 110, 112. The app may include a navigation application (app) for running the surgical plan, including detecting the 2D code 222 and presenting one or more holograms. In some embodiments, a planning app may be loaded on the AR headsets 110, 112 so that one or more of the holograms can be updated dynamically from the AR headsets 110, 112.

The app may be controlled through user interface elements provided the AR headsets 110, 112, such as hand gestures for opening and interfacing with applications. In other embodiments, a surgeon may control and/or operate the app using verbal commands. For example, in response to a first verbal command, e.g., "load", the app may automatically open a file explorer window. The surgeon can then select a hologram file in a subfolder with a hand gesture. The app may automatically pick up a transformation matrix for the hologram, which may also be located in the same folder, identify the physical 2D code in the surgical scene, and anchor the hologram. In other embodiments, the surgeon can use other verbal commands to cause the AR headsets 110 and 112 to load and present additional holograms. Exemplary verbal commands include "hologram2", "hologram3", etc. for presenting the holograms in the planned order for the surgical procedure.

Surgical Procedure

The surgeon may determine one or more initial (pre-operative) patient measurements, such as leg length and/or offset. A suitable technique for measuring these values, and for performing a trial reduction of an artificial hip is described in U.S. Pat. No. 7,885,705, issued Feb. 8, 2011, for a SYSTEM AND METHOD FOR FACILITATING HIP SURGERY, which is hereby incorporated by reference in its entirety.

Registration of the Pelvis.

If the surgical plan incorporated a registration instrument 200, 700, then the instrument 200, 700 may be adjusted for the patient as pre-operatively determined during the planning stage. For example, the legs of the registration instrument 200, 700 may be adjusted relative to each other, as pre-operatively determined for the specific patient. Once the registration instrument 200, 700 has been adjusted in accordance with the pre-operative plan, the registration instrument 200, 700 may be docked, e.g., attached, to the patient according to the plan, e.g., to the patient's pelvis. For example, the plan may specify the points, e.g., three points, at which the tips of the legs of the registration instrument 200, 700 are to be docked to the patient's pelvis.

For the registration instrument 200, the first and second points may be readily identified by the surgeon during the procedure. The surgeon may not, however, directly identify the location of the third point. Instead, the tip of the third leg 204*b* may land at the third point after the tips 216*a* and 216*c* of the first and second legs 204*a* and 204*c* are placed at the first and second points on the patient's pelvis.

In some embodiments, the surgeon may use other instruments, such as one or more jigs, drill guides, patient-specific or non-patient specific templates, etc., to locate the basepoint for receiving the tip 216*a* of the first leg 204*a* of the registration instrument 200. In addition, the distance between the tip 216*a* of the first leg 204*a* of the instrument 200 and the tip 216*c* of the second leg 204*c* of the instrument 200 may be set to a desired distance and locked, thereby assisting the surgeon in locating the second point, given that the second point is a constrained distance from the first point. By having or setting the tip 216*c* of the second leg 204*c* to a prescribed distance from the tip 216*a* of the first leg 204*a*, any error in locating the second point may be reduced.

In some embodiments, the surgeon may adjust the instrument 200, 700 as it is being docked to the patient's pelvis so that the tips of the legs contact the planned points on the patient's pelvis.

Basepoint Inside the Acetabulum

In some embodiments, the basepoint may be located inside the acetabulum. Such embodiments may be well suited for the anterolateral and anterior approaches of total hip replacement (THR). More specifically, a posterior location of the acetabulum may be selected during the pre-operative planning stage for the basepoint location. Nonetheless, it should be understood that other locations within the acetabulum, besides a posterior location, may be utilized as the basepoint for the registration instrument. For example, a central point on the surface of the acetabulum may be selected for the basepoint location. During the procedure, one or more instruments may be used by the surgeon to locate the pre-selected posterior location for basepoint in the patient's acetabulum.

If the instrument 700 is being used during surgery, the first moveable leg brace 706 and the second moveable leg brace 708 of the instrument 700 may be adjusted as planned so that the tips 726, 730 of the respective legs 714, 716 contact the patient's pelvis at the planned locations. The instrument 700 may be docked to the patient's pelvis 702. The AR headsets 110 and 112 may detect the one or more 2D codes on the target plate 734 and may anchor one or more holograms as described herein.

With the instrument 200, 700 including the target plate 300, 734 docked to the patient's pelvis as planned, the surgeons 106 and 108 may activate their AR headsets 110 and 112. The surgeons may launch the planning or navigation app on the AR headsets 110 and 112. The AR headsets 110 and 112 may search image or other data captured by the AR headsets 110 and 112 for the 2D code 222, 740 on the target plate 300, 734 of the physical registration and tracking instrument 200, 700 docked to the patient's pelvis. Upon detecting a 2D code, the AR headsets 110 and 112 recover the spatial coordinate system of the detected 2D code. The AR headsets 110 and 112 may also access the transformation matrix for the detected 2D code. The AR headsets 110 and 112 may continuously track the detected 2D code throughout the surgical procedure. For example, one or more sensors on the AR headsets 110 and 112 may track the detected 2D according to a frame rate, such as 60 frames per second.

Presentation of Holograms

Utilizing the spatial coordinate system and the transformation matrix, the AR headsets 110 and 112 may present a hologram of the instrument 200, 700 that is co-located, e.g., spatially aligned, with the physical instrument 200, 700 docked to the patient's pelvis. The AR headsets 110 and 112 may also provide an indication that they have detected the 2D code 222, 740 and are tracking it. For example, a green light may be presented by the AR headsets 110 and 112 to confirm detection and tracking of the 2D code 222, 740. Once the AR headsets 110 and 112 have detected and are tracking a 2D code, the lead surgeon, e.g., surgeon 106 may operate the AR headset 110 to present the holograms developed for the surgical plan. In some embodiments, when the application on the AR headset 110 opens, the surgeon 106 may identify, e.g., point to, a folder created for the patient that includes all planned holograms in the sequence of the procedure.

As described herein, during the surgical procedure, the AR headsets 110 and 112 may detect the 2D code 222 integrated with the target plate 300 of the instrument 200 that is docked to the patient's pelvis. The AR headsets 110 and 112 may utilize the spatial coordinate system associated with the detected 2D code and the patient-specific transformation matrix to position the holograms of the surgical plan. The AR headsets 110 and 112 may anchor the holograms relative to the spatial coordinate system for the detected 2D code. In some embodiments, the patient-specific transformation matrix may be stored with the holograms. The transformation matrix with the 2D codes may be hard coded in the application. In other embodiments, it may be stored in one or more folders. When the AR headsets 110 and 112 access a hologram, e.g., from the folder, for presentation, the AR headsets 110 and 112 may also retrieve the patient-specific transformation matrix.

It should be understood that one or more of the holograms do not need to include the registration instrument 200, 700. However, by including a hologram of the instrument 200, 700, there is a constant visual confirmation to the surgeons 106, 108 that the anchoring is correct, e.g., because the physical instrument 200, 700, which is outside of the patient's body is co-located with the hologram of the instrument.

In some embodiments, the registration instrument 200, 700 may remain docked to the patient's pelvis throughout the surgical procedure. In other embodiments, the registration of the patient's anatomy, e.g., the pelvis, by the instrument 200, 700 may be transferred from the instrument 200, 700 to another instrument or device, thereby allowing removal of the instrument 200, 700 while the surgical procedure is continued. Removal of the instrument 200, 700 may provide easier access to the surgical site.

Figure 8:
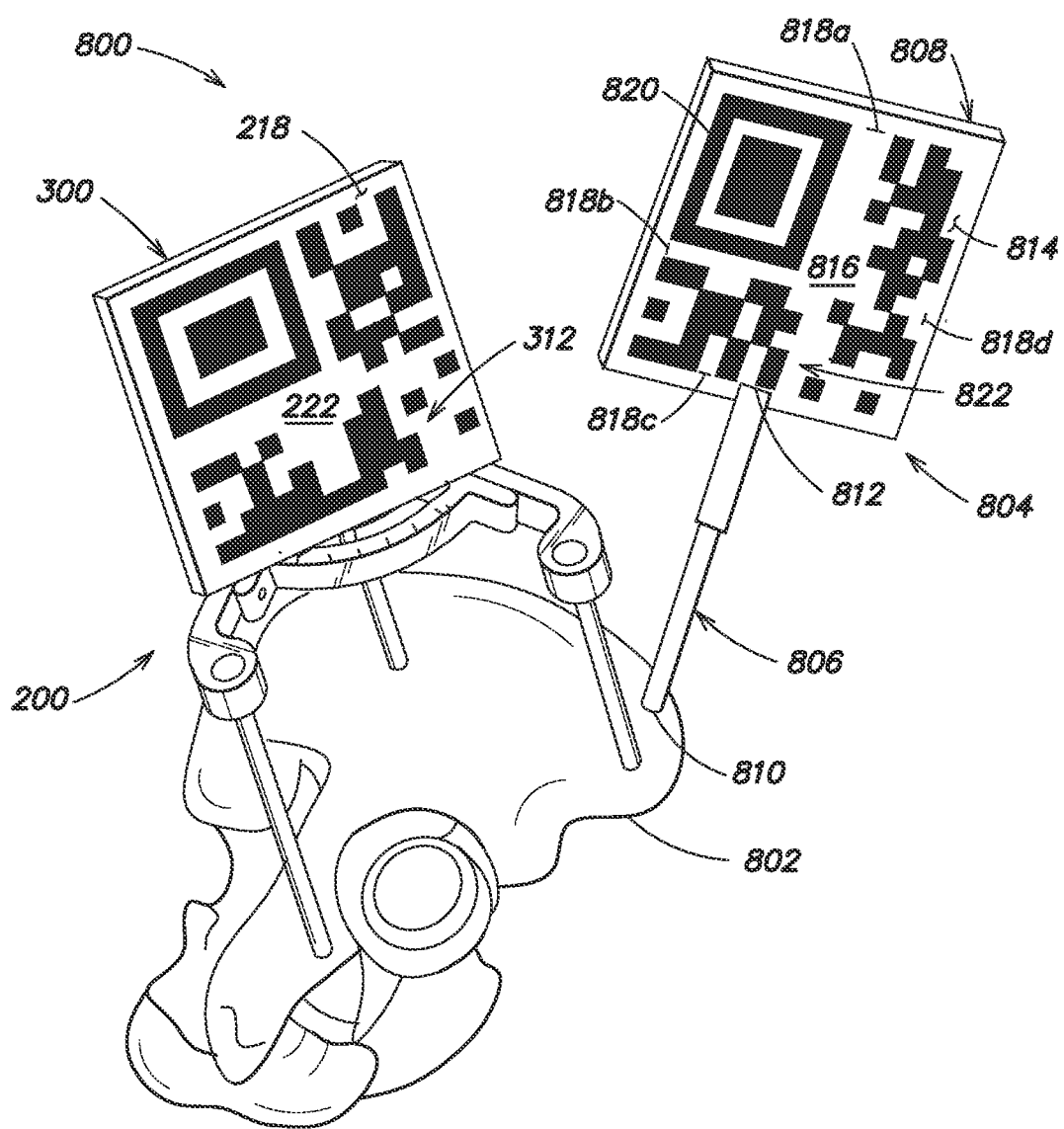
FIG. 8 is a schematic illustration of a portion of a surgical scene in accordance with one or more embodiments.

FIG. 8 is a perspective view of an arrangement 800 of instruments permitting continued navigation following removal of the instrument 200 in accordance with one or more embodiments. A tracker tool 804 may be attached to the patient's pelvis in a random location and orientation. That is, the tracker tool 804 may be attached anywhere to the pelvis 802, such as a point that is accessible to the surgeons 106 and 108 through the incision. The tracker tool 804 may include a support element 806 and a target plate 808. The support element 806, which may be in the form of a pin or rod, may include one end 810 configured for attachment to the patient's anatomy, e.g., the patient's pelvis, and a second end 812 to which the target plate 808 may be attached. The target plate 808 may include a front face 814 and a back face (not shown). A 2D code indicated at 816 may be presented on the front face 814 of the target plate 808. Another 2D code that is different that the 2D code 816 may be presented on the back face of the target plate 808.

The instrument 200 may then be docked to the pelvis 802 as planned. The AR headsets 110 and 112 may detect and track the 2D code 222, thus registering the pelvis 802 in space.

In some embodiments, the 2D code 816 of the tracker tool 804 may have the same structure as the 2D code 222 presented on the target plate 300 of the instrument 200. For example, the 2D code 816 may include a quiet zone or border indicated at 818a-d, a positioning detection marker 820, and a detection pattern indicated at 822. However, the detection pattern 822 of the 2D code 816 of the target plate 808 of the tracker tool 804 is different than the detection pattern 312 of the 2D code 222 of the target plate 300 of the instrument 200. Because the detection patterns 312 and 822 are different, the navigation app running the AR headsets 110 and 112 is able to distinguish between the 2D codes 222 and 816 and thus between the instrument 200 and the tracker tool 804.

A spatial coordinate system may also be associated with the 2D code 816 of the tracker tool 804. For example, the spatial coordinate system may have an origin at the center of the target plate 808 and may define x, y, and z axes in a similar manner as described in connection with the 2D code 222 of the target plate 300.

The target plate 804 may have substantially the same dimensions as the target plate 300 and may be fabricated in substantially the same manner.

During the surgical procedure, the app running on the AR headsets 110 and 112 may be configured to detect and track the 2D code 222 of the target plate 300 of the instrument 200. That is, even though the AR headsets 110 and 112 recognize both 2D codes 222, 816, the navigation app detects and tracks the 2D code 222 of the instrument 200. However, in response to a command by the surgeon 106, the AR headsets 110 and 112 may switch from tracking the 2D code 222 to tracking the 2D code 816 of the tracker tool 804. For example, the surgeon may provide a gesture or a voice command, such as "switch". In response to the command, the navigation app may detect the 2D code 816 of the tracker tool 804 and derive the spatial coordinate system defined for the 2D code 816. The app may then generate a transformation matrix to translate between the one or more reference coordinate systems used during the planning stage, e.g., the AP plane for the pelvis 802, and the spatial coordinate system associated with the 2D code 816 of the tracker tool 804 as randomly attached to the pelvis 702. For example, the navigation app may determine where the spatial coordinate system of the 2D code 816 of the tracker tool 804 is in space relative to the one or more reference coordinate systems (or alternatively or additionally relative to the spatial coordinate system of the 2D code 222 of the target plate 300). The navigation app may use the position of the spatial coordinate system of the 2D code 816 to generate the transformation matrix. Once the transformation matrix is generated, the app may utilize the generated transformation matrix to present and anchor one or more holograms of the surgical plan. In some embodiments, the navigation app may present an indication to the surgeons 106 and 108 that the transformation matrix for the tracker tool 804 has been generated and detection and tracking of the 2D code 816 is proceeding.

At this point the target plate 300 of the instrument 200 is no longer necessary to present and anchor the holograms. Accordingly, the instrument 200 may be removed, e.g., undocked from the patient's pelvis 802 and set aside. The app may then use the tracking tool 804 to perform further registration and tracking of the pelvis 802 during the surgical procedure.

If the instrument 200 is left docked to the patient's pelvis, the surgeon 106 can switch the navigation back to the 2D code 222 of the instrument 200. For example, the surgeon can enter a command, e.g., the "switch" command. In response, the navigation app may detect the 2D code 222, access the transformation matrix for the 2D code 222 are resume presentation and anchoring of holograms using the 2D code 222 and its transformation matrix.

Figure 9:
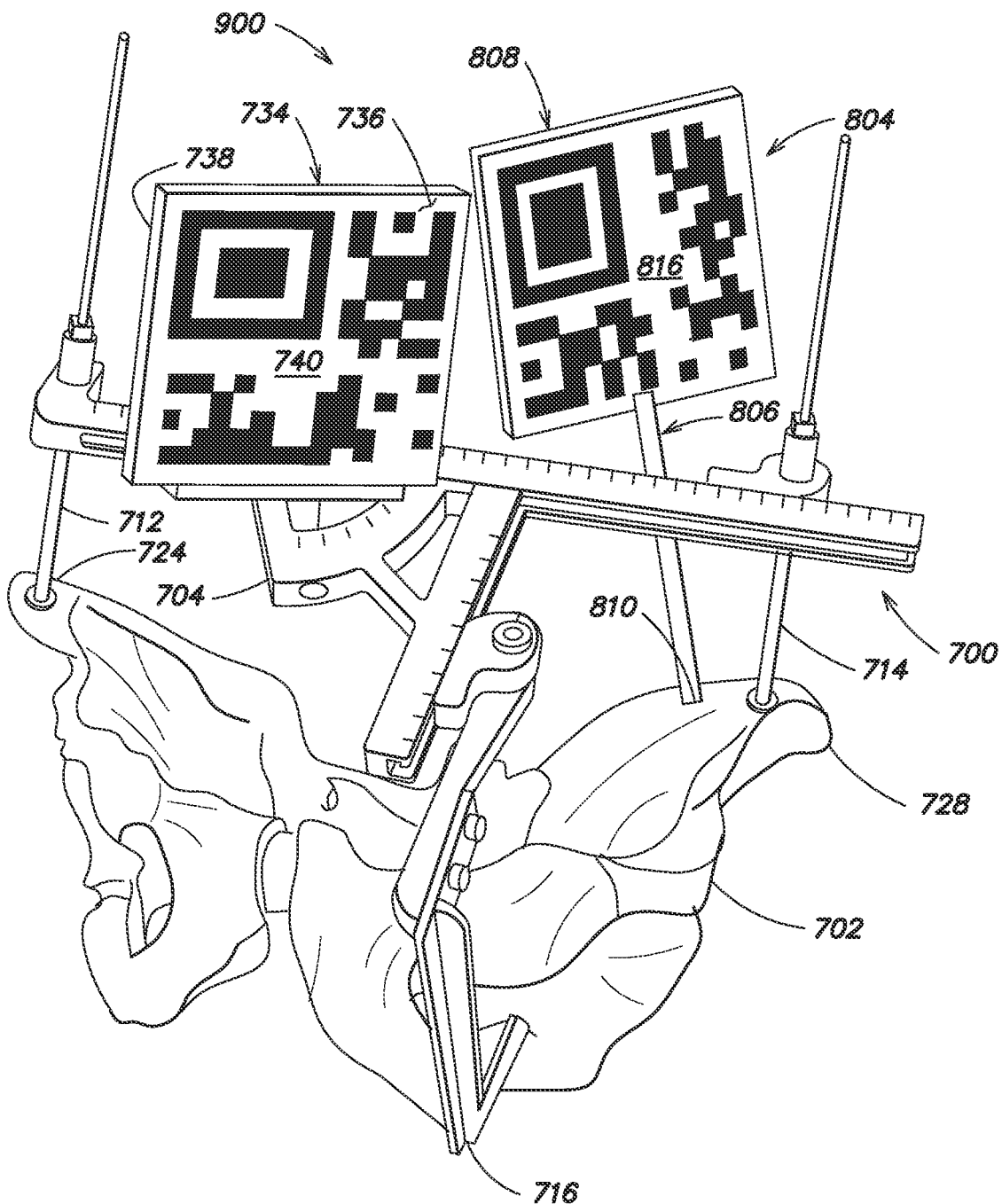
FIG. 9 is perspective view of a tracker tool in accordance with one or more embodiments.

FIG. 9 is a perspective view of an arrangement 900 of instruments permitting continued navigation following removal of the instrument 700 in accordance with one or more embodiments. The tracker tool 804 may be attached to the patient's pelvis 702 in a random location and orientation. That is, the tracker tool 804 may be attached anywhere to the pelvis 702, such as a point that is accessible to the surgeons 106 and 108. The instrument 700 may then be docked to the pelvis 702 as planned. The AR headsets 110 and 112 may detect and track the 2D code 740, thus registering the pelvis 702 in space.

The surgeon 106 may then direct the navigation app running on the AR headsets 110 and 112 to switch navigation from the 2D code 740 of the instrument 700 to the 2D code 816 of the tracker tool 804. For example, the surgeon 106 may enter the "switch" voice command. In response to the command, the navigation app may detect the 2D code 816 of the tracker tool 804 and derive the spatial coordinate system defined for the 2D code 816. The app may then generate a transformation matrix to translate between the one or more reference coordinate systems used during the planning stage, e.g., the AP plane for the pelvis 802, and the spatial coordinate system associated with the 2D code 816 of the tracker tool 804 as randomly attached to the pelvis 902.

The navigation app may use the position of the spatial coordinate system of the 2D code 816 relative to the one or more reference coordinate systems and/or the spatial coordinate system associated with the 2D code 740 of the instrument 700 to generate the transformation matrix. Once the transformation matrix is generated, the app may utilize the spatial coordinate system associated with the 2D code 816 and generated transformation matrix to present and anchor one or more holograms of the surgical plan. Accordingly, the instrument 700 may be removed and navigation continued, e.g., the presentation of the planned holograms, based on the 2D code 816 of the tracker tool 804.

While embodiments have been described in connection with the 2D codes presented on the front faces of the target plates, e.g., target plates 300, 734, 808, it should be understood that the 2D codes on the back faces may be used in the same manner. For example, the AR headsets 110 and 112 may detect and track the 2D codes on the back faces of the target plates. If two target plates are present, the AR headsets 110 and 112 may switch between any combination of 2D codes on the front and back surfaces of the target plates.

Other Instruments/Tools

It should be understood that the target plate of the present disclosure may be used with other surgical instruments and/or tools. For example, the target plate may be used with a digitizer probe used to digitize, e.g., obtain the three dimensional coordinates of a point on the patient's anatomy, such as a point on the patient's pelvis. For example, a target plate, such as the target plate 808, may be mounted to a pin having a tip. Based on the construction of the digitizer, the location of the tip is known relative to the spatial coordinate system defined for the 2D code on the target plate of the digitizer. The tip of the digitizer may be placed at a point whose coordinates are desired. a command may be entered to the AR headsets 110 and 112. The navigation app may compute the coordinates of the tip and thus the point on the patient's anatomy based on the spatial coordinate system of the 2D code used on the digitizer, which may be detected and tracked by the AR headsets 110 and 112. The coordinates of the tip and the point on the patient's anatomy may be translated to another coordinate system, such as the one or more reference coordinate system using a transformation matrix generated for the 2D code of the digitizer.

The target plate may also be used on surgical tools, such as cup impactors, reamers, etc.

The foregoing description has been directed to specific embodiments of the present disclosure. It will be apparent, however, that other variations and modifications may be made to the described embodiments, with the attainment of some or all of their advantages. Therefore, it is the object of the appended claims to cover all such variations and modifications as come within the true spirit and scope of the invention.

What is claimed is:

1. A registration and tracking device comprising:
   a support bar having first and second ends and a longitudinal axis;
   a platform slidably attached to the support bar;
   a first leg removably attached proximate to the first end of the support bar;
   a second leg removably and adjustably attached proximate to the second end of the support bar, where the second leg is adjustable in a direction along the longitudinal axis;
   a third leg removably attached to the platform, where the third leg is adjustable in a direction orthogonal to the longitudinal axis; and
   a target plate attached to the platform opposite the first, second, and third legs, wherein
      the target plate defines a front face and a back face,
      the target plate includes a two-dimensional code at the front face,
      the two-dimensional code is free from including one or more alignment markings,
      the two-dimensional code defines a three-dimensional spatial coordinate system,
      the two-dimensional code is integrated with the target plate,
      the support bar and the platform define a nominal plane, and
      the target plate is in a known geometric relationship to the nominal plane.

2. The registration and tracking device of claim 1 wherein the target plate is black anodized and the two-dimensional code is formed by laser etching the front face.

3. The registration and tracking device of claim 2 wherein the laser etching produces pixel elements by removing the black anodize and the pixel elements form the two-dimensional code.

4. The registration and tracking device of claim 3 wherein the target plate is four inches by four inches and the two-dimensional code has fewer than 20 by 20 of the pixel elements.

5. The registration and tracking device of claim 4 wherein the two-dimensional code is a fourteen-by-fourteen array of the pixel elements.

6. The registration and tracking device of claim 4 wherein the two-dimensional code includes:
   a quiet zone around an outer perimeter of the two-dimensional code;
   a positioning detection marker; and
   a detection pattern.

7. The registration and tracking device of claim 6 wherein the two-dimensional code is further free from including:
   one or more timing patterns;
   version information;
   format information; and
   one or more error correction codes.

8. The registration and tracking device of claim 7 wherein the detection pattern does not encode data.

9. The registration and tracking device of claim 2 wherein the target plate is formed from aluminum.

10. The registration and tracking device of claim 1 wherein
    the target plate includes a second two-dimensional code at the back face, and
    the second two-dimensional code is integrated with the target plate.

11. A system comprising:
    a registration and tracking device including:
       a support bar having first and second ends and a longitudinal axis;
       a platform slidably attached to the support bar;
       a first leg removably attached proximate to the first end of the support bar;

a second leg removably and adjustably attached proximate to the second end of the support bar, where the second leg is adjustable in a direction along the longitudinal axis;

a third leg removably attached to the platform, where the third leg is adjustable in a direction orthogonal to the longitudinal axis;

a target plate attached to the platform of the registration and tracking device opposite the first, second, and third legs, wherein the target plate defines a front face and a back face, the target plate includes a two-dimensional code at the front face, the two-dimensional code defines a three-dimensional spatial coordinate system, the two-dimensional code is integrated with the target plate, the support bar and the platform define a nominal plane, and the target plate is in a known geometric relationship to the nominal plane; and a mixed reality (MR) head-mounted device (HMD) configured to:

detect the two-dimensional code at the front face of the target plate;

utilize a transformation matrix to determine a position for a hologram relative to the three-dimensional spatial coordinate system defined by the two-dimensional code of the target plate; and project the hologram at the determined position relative to the three-dimensional spatial coordinate system defined by the two-dimensional code at the front face of the target plate, wherein the MR HMD detects the two-dimensional code and projects the hologram without utilizing one or more two-dimensional code alignment markings.

12. The system of claim 11 wherein the target plate is black anodized and the two-dimensional code is formed by laser etching the front face.

13. The system of claim 12 wherein the laser etching produces pixel elements by removing the black anodize and the pixel elements form the two-dimensional code.

14. The system of claim 13 wherein the target plate is four inches by four inches and the two-dimensional code has fewer than 20 by 20 of the pixel elements.

15. The system of claim 13 wherein the two-dimensional code integrated with the target plate includes:

a quiet zone around an outer perimeter of the two-dimensional code;

a positioning detection marker; and a detection pattern.

16. The system of claim 15 wherein the two-dimensional code integrated with the target plate is free from including:

the one or more alignment markings;

one or more timing patterns;

version information;

format information; and one or more error correction codes.

17. The system of claim 11 wherein the target plate includes a second two-dimensional code at the back face, the second two-dimensional code is integrated with the target plate, and the MR HMD detects either the two-dimensional code at the front face or the second two-dimensional code at the back face.

18. A method comprising:

docking a registration and tracking device to a portion of a patient's anatomy, wherein the registration and tracking device includes a support bar having first and second ends and a longitudinal axis, a platform slidably attached to the support bar, wherein the support bar and the platform define a nominal plane, a first leg removably attached proximate to the first end of the support bar, a second leg removably and adjustably attached proximate to the second end of the support bar, where the second leg is adjustable in a direction along the longitudinal axis;

a third leg removably attached to the platform, where the third leg is adjustable in a direction orthogonal to the longitudinal axis; and a target plate attached to the platform opposite the first, second, and third legs in a known geometric relationship to the nominal plane, the target plate having a front face;

detecting, by a mixed reality (MR) head-mounted device (HMD), a two-dimensional code at the front face of the target plate, wherein the two-dimensional code (i) is integrated with the target plate, and (ii) defines a three-dimensional spatial coordinate system;

utilizing, by the MR HMD, a transformation matrix to determine a position for a hologram relative to the three-dimensional spatial coordinate system defined by the two-dimensional code of the target plate; and projecting, by the MR HMD, the hologram at the determined position relative to the three-dimensional spatial coordinate system defined by the two-dimensional code at the front face of the target plate, wherein the detecting the two-dimensional code and the projecting the hologram is free from utilizing one or more two-dimensional code alignment markings.

19. The method of claim 18 wherein the target plate of the registration and tracking device is black anodized, the two-dimensional code is formed by laser etching the front face, the laser etching produces pixel elements by removing the black anodize, and the pixel elements form the two-dimensional code.

20. The method of claim 19 wherein the target plate is four inches by four inches, the two-dimensional code has fewer than 20 by 20 of the pixel elements, the two-dimensional code includes:

a quiet zone around an outer perimeter of the two-dimensional code;

a positioning detection marker; and a detection pattern, the two-dimensional code is free from including:

the one or more alignment markings;

one or more timing patterns;

version information;

format information; and one or more error correction codes.

* * * * *